United States Patent [19]

Arnott et al.

[11] Patent Number: 5,330,817
[45] Date of Patent: Jul. 19, 1994

[54] INCONTINENCE PAD

[75] Inventors: Robert C. Arnott; James P. Cain, both of Spartanburg, S.C.

[73] Assignee: Milliken Research Corporation, Spartanburg, S.C.

[21] Appl. No.: 351,385

[22] Filed: May 15, 1989

[51] Int. Cl.⁵ .............................................. B32B 33/00
[52] U.S. Cl. ..................................... 428/85; 428/246; 428/253; 428/286
[58] Field of Search ................. 428/85, 246, 252, 298, 428/296, 253; 604/358, 367, 378, 368, 375

[56] References Cited

U.S. PATENT DOCUMENTS

| | | | |
|---|---|---|---|
| 3,349,769 | 10/1967 | Piekarski | 604/375 |
| 3,563,243 | 1/1971 | Lindquist | 604/369 |
| 3,888,256 | 6/1975 | Studinger | 428/87 |
| 3,967,623 | 7/1976 | Butterworth et al. | 604/370 |
| 4,097,943 | 7/1978 | O'Connell | 5/484 |
| 4,128,686 | 12/1978 | Kyle et al. | 428/219 |
| 4,216,774 | 8/1980 | Graber | 604/371 |
| 4,352,356 | 10/1982 | Tong | 604/402 |
| 4,496,358 | 1/1985 | Karami et al. | 604/379 |
| 4,578,070 | 3/1986 | Holtman | 604/378 |
| 4,622,036 | 11/1986 | Goodrum | 428/314.2 |
| 4,655,877 | 4/1987 | Horimotr et al. | 428/296 |
| 4,659,614 | 4/1987 | Vitale | 428/286 |
| 4,681,577 | 7/1987 | Stern et al. | 604/368 |
| 4,685,914 | 8/1987 | Holtman | 604/367 |
| 4,699,808 | 10/1987 | Menard et al. | 427/180 |
| 4,718,899 | 1/1988 | Itoh et al. | 604/375 |
| 4,772,281 | 9/1988 | Armstead | 604/378 |
| 4,844,965 | 7/1989 | Foxman | 428/246 |

Primary Examiner—Jenna L. Davis
Attorney, Agent, or Firm—Terry T. Moyer; Earle R. Marden

[57] ABSTRACT

A three-ply incontinence pad sewn together at the edges thereof. The plies consist basically of (1) a pile terry circular knit upper ply bonded to a (2) nonwoven soaker ply which are sewn to a bottom ply constituted by a woven fabric on which is laminated or coated a thermoplastic film to act as a barrier.

2 Claims, 1 Drawing Sheet

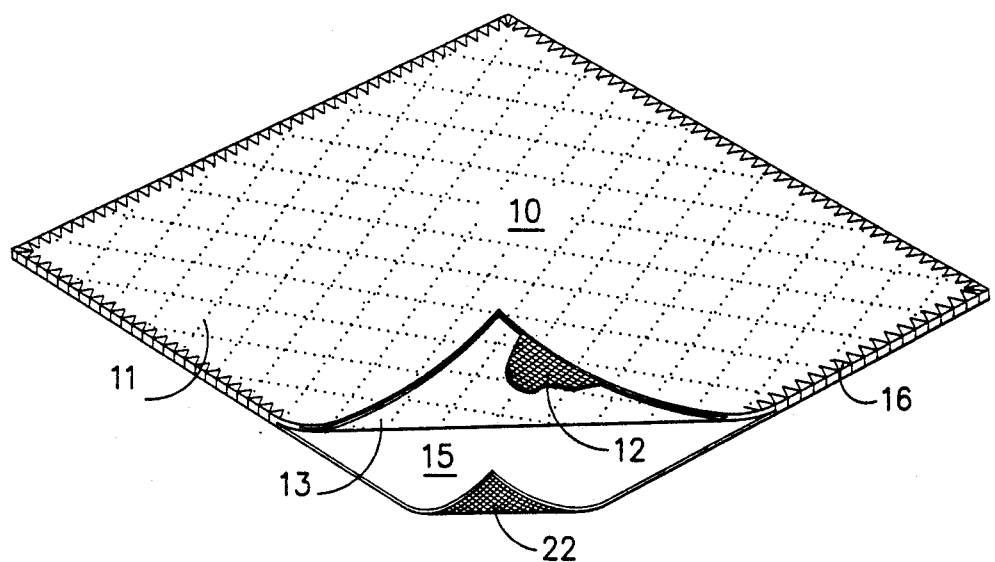
FIG. -1-
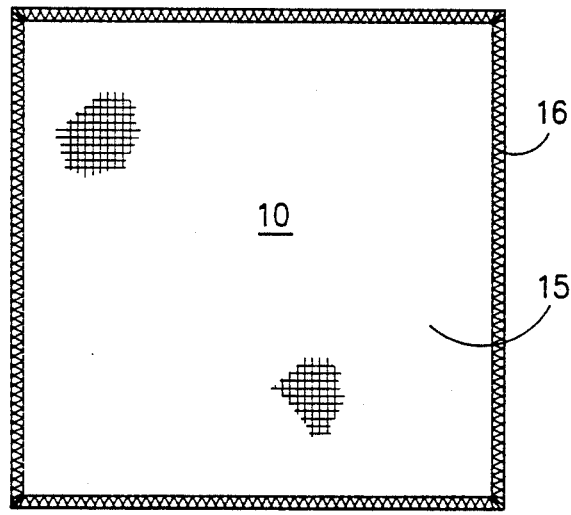
FIG. -2-
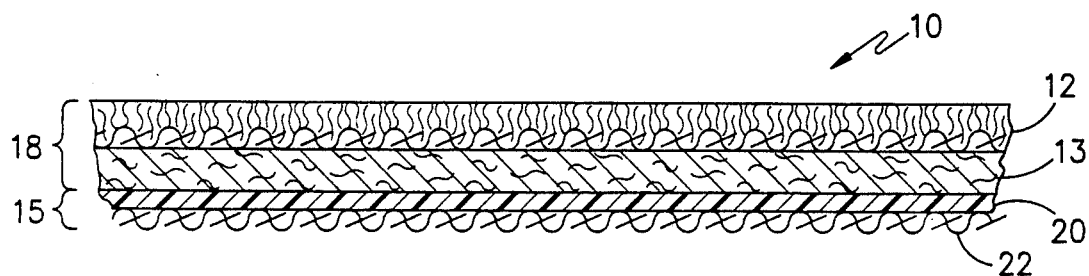
FIG. -3-

INCONTINENCE PAD

The present invention relates to a reusable absorbent pad for use in hospitals and nursing homes beneath patients who are incontinent or who might otherwise have the need for an absorbent and protective component of their bedding.

The problem of incontinence in seriously ill or elderly patients at home, in hospitals, and in nursing homes is well recognized by health care professionals. Many products have been developed and marketed for use in protecting patients' bedding from damage caused by absorption of urine and other fluids. Minimizing patient irritation and discomfort caused by prolonged exposure to absorbed fluids is also a concern of those caring for the patient.

Disposable underpads are currently used by many institutions but are relatively expensive and do not provide optimum comfort and absorption because of the types of material s that must be used. Consequently multiple pads are used under the patient at each change which gives better protection to the bedding but does little to aid patient comfort.

Reusable underpads previously known in the industry suffer from a number of drawbacks. A significant problem in reusable pads currently available is durability to withstand exposure to the soap, bleach, alkalinity and high temperature of the wash and dry cycles in an industrial or institutional laundry. It must be recognized that home wash conditions are much milder. For a valid comparison as to durability, competitive pads must be washed under the same conditions. The pad disclosed by the present invention will withstand a minimum of 175 industrial launderings while the best of the currently available products suffer significant breakdown at 100 washings or less. Similarly, the various combinations of materials and bonding techniques used on the prior art have not resulted in optimum performance characteristics. The surface of the top fabric of the composite, that portion against the skin, should have a soft comfortable texture and aid in conducting fluid into the interior of the structure. The absorbent middle layer must spread and contain the fluid, and must resist releasing it back to the patient even under pressure from the patient's body weight. The bottom layer must not slide on the bed, making it difficult to keep the pad in position and the whole structure must be strong enough to support the weight of the patient since nurses often use the pads to turn the patient. The bottom layer is also the barrier, and must not allow fluid to pass through it into the bed linens underneath. The pad disclosed by this invention satisfies these requirements.

It is therefore an object of the invention to provide an incontinent pad which is durable and provides maximum comfort to the patient with minimum difficulty and expense to the patient and/or personnel attending the patient.

Other objects and advantages of the invention will become readily apparent as the specification proceeds to describe the invention with reference to the accompanying drawing, in which:

FIG. 1 is a partial perspective view of the new and improved incontinent pad with parts broken away to show the interior thereof;

FIG. 2 is a bottom view of the pad shown in FIG. 1, and

FIG. 3 is a cross-section view of the pad of FIG. 1 showing the layers thereof in detail.

Looking now to the drawing, the new incontinent pad is represented by the reference number 10 and consists basically of the top fabric 18 and the bottom fabric 15 sewn or otherwise secured at 16 around the edges thereof to provide a unitary structure.

The upper or top fabric 18, in the preferred form of the invention, consists basically of a napped, terry circular knit polyester fabric 12 ultra-sonically bonded along lines 11 to a needlepunched polyester acrylic intimate blend nonwoven fabric 13. The fabric 12 has a single ply, 150 denier, 68 filament polyester loop yarn with a single ply, 100 denier, 34 filament back yarn and a weight of 5.5 oz/yd . The fabric 13 is a 70/30 polyester/acrylic blend needlepunched to hold it together with a weight of $8\frac{1}{2}$ oz/yd$^2 \pm \frac{1}{2}$oz/yd$^2$.

The pile and construction of the fabric 12 provides ready passage of urine and other fluids into the soaker fabric 13 but resists the reverse passage of the urine back to the patient's skin thereby preventing discomfort to the patient. The soaker fabric 13 is made preferably of 3 to 4 inch staple and is heatset to provide resistance to pilling and fiber loss and promotes diffusion of liquid passed into it from the fabric 12. The particular 70/30 polyester/acrylic blend enhances the diffusion of the liquid throughout the fabric 13. The soaker layer 13 is in weights from 5 oz/yd$^2$ to 17 oz/yd$^2$ (2 layers of 8.5 oz/yd$^2$ fabric) designed for wheel chair pads with smaller surface area. The needle punch density was 1140 punches/in$^2$.

The lower or bottom fabric 15 consists basically of a 2×1 oxford woven polyester fabric 22 having a 4 mil barrier film 20 of polyvinylchloride coated or laminated thereto. The fabric 22 was woven with a two-ply, 150 denier, 68 filament polyester warp yarn and a two-ply, 150 denier, 68 filament polyester fill yarn and has a weight of 6.03 oz/yd$^2$. The film 20 has a weight in the range of 4–6 oz/yd$^2$.

The film 20 provides a barrier against the passage of liquid and/or urine through the pad 10 onto the sheets and/or bed underneath. The bottom woven fabric 22 is of such a construction to provide stability and durability to the pad 10 and at the same time allows the pad 10 to be readily slid or moved around under the patient. If desired, the fabric 12 can be treated to provide cleanability and soil release to enhance the appearance of the pad. The pad 10 can be made in any suitable size such as 18"×18", 24"×30", 30"×36", 36" etc.

A prime consideration of an incontinence pad is to eliminate or reduce the tendency of liquid or urine to wet back through the fabric 12 to the clothes and/or skin of the patient. To test the disclosed pad the following wet back test was employed. The test was performed on pads that had been washed up to 150 cycles in a Milnor industrial washer using a formulated known in the industry as linen white with bleach.

WET BACK TEST

Place a pad 10 onto a flat, Teflon coated plate. Suspend a burette over the pad at a height of 6 inches. Fill the burette with distilled water for each test. Water flow therefrom should be approximately 1 ml/second. Deliver the water onto the pad. Wait one minute after the flow has ceased then center a double layer of 12"×12" A$^2$TC$^2$ blot paper which has been preweighed over the point of impact. Place a 29.6 pound weight with a 12"×12" base on the blot paper to simulate a body weight. After thirty (30) seconds remove and weigh the blot paper. Subtract the dry weight of the blot paper from the wet weight of the blot paper after the above noted 30 seconds to provide the amount of water wet back through the fabric 12.

| Number of Washes | ml of Water introduced | ml returned from the pad | % Retained |
| --- | --- | --- | --- |
| 25 | 50 | 11 | 78% |
| 25 | 100 | 13 | 87% |
| 25 | 150 | 10 | 93% |
| 50 | 50 | 11 | 78% |
| 50 | 100 | 20 | 80% |
| 50 | 150 | 32 | 78% |
| 95 | 50 | 14 | 72% |
| 95 | 100 | 24 | 76% |
| 95 | 150 | 37 | 75% |
| 150 | 50 | 12 | 76% |
| 150 | 100 | 20 | 80% |
| 150 | 150 | 34 | 77% |

As herein described the disclosed incontinence pad has numerous advantages. The reduced wet back trait provides more comfort to the patient, reduces the amount of work required by the attendants, reduces the amount of bed linen needed because there is no runoff with insult levels up to 500 ml. All of these reductions substantially reduce the cost since fewer pads are necessary along with the above-noted ancillary savings.

Although the preferred embodiment of the invention has been described specifically, it is contemplated that changes may be made without departing from the scope or spirit of the invention and it is desired that the invention be limited only by the scope of the claims.

We claim:

1. A reusable incontinance pad comprising a top layer of circular knit terry fabric, an absorbent layer below said top layer being composed of a 70/30 blend of polyester/acrylic nonwoven fabric and a water impervious layer below said absorbent layer, all of said layers being connected together to form a unitary structure.

2. The pad of claim 1 wherein said water impervious layer is polyester woven fabric having a thermoplastic film on the top thereof adjacent said absorbent layer.

* * * * *